: US 8,529,670 B2
(45) Date of Patent: Sep. 10, 2013

(12) United States Patent
Sangi (54) ASEPTIC BOTTLING OR CONTAINER FILLING PLANT WITH A CLEAN ROOM ARRANGEMENT ENCLOSING THE ASEPTIC BOTTLING OR CONTAINER FILLING PLANT AND A FILTER UNIT FOR FILTERING AIR ENTERING THE CLEAN ROOM, AND A METHOD OF OPERATION THEREOF (75) Inventor: Daryoush Sangi, Hamburg (DE)

(73) Assignee: KHS GmbH, Dortmund (DE)

( * ) Notice: Subject to any disclaimer, the term of this patent is extended or adjusted under 35 U.S.C. 154(b) by 512 days.

(21) Appl. No.: 12/364,971

(22) Filed: Feb. 3, 2009

(65) Prior Publication Data

US 2010/0032055 A1 Feb. 11, 2010

Related U.S. Application Data (63) Continuation-in-part of application No. PCT/EP2007/006806, filed on Aug. 1, 2007.

(30) Foreign Application Priority Data

Aug. 4, 2006 (DE) .......................... 10 2006 036 476

(51) Int. Cl.
*B01D 46/00* (2006.01)
(52) U.S. Cl.
USPC ............. 95/273; 55/385.2; 55/385.1; 55/485; 55/486; 55/497; 55/318; 55/327; 55/471; 55/473; 55/480; 55/482; 55/505; 55/DIG. 18; 95/283; 95/287; 96/226; 96/227; 422/28; 422/120

(58) Field of Classification Search
USPC ...... 55/385.2, 385.1, 485, 486, 497, DIG. 18, 55/318, 327, 471, 473, 480, 482, 505; 95/285, 95/287, 90, 148; 96/108, 143, 134, 147, 96/223, 222, 224, 225; 454/53, 187; 422/122
See application file for complete search history.

(56) References Cited

U.S. PATENT DOCUMENTS

| 4,707,167 A | * | 11/1987 | Saito et al. ...................... 96/225 |
| 5,488,811 A | * | 2/1996 | Wang et al. ........................ 53/52 |
| 5,626,820 A | * | 5/1997 | Kinkead et al. ................ 422/122 |
| 5,711,705 A | * | 1/1998 | Krainiak et al. ................. 454/57 |
| 6,102,977 A | * | 8/2000 | Johnson ....................... 55/385.2 |

(Continued)

FOREIGN PATENT DOCUMENTS

| DE | 18 15 538 | 11/1969 |
| DE | 26 31 260 | 1/1978 |

(Continued)

OTHER PUBLICATIONS

English Translation of International Preliminary Report on Patentability PCT/EP2007/006806.

(Continued)

*Primary Examiner* — Duane Smith
*Assistant Examiner* — Minh-Chau Pham
(74) *Attorney, Agent, or Firm* — Nils H. Ljungman & Associates (57) ABSTRACT

Aseptic bottling or container filling plant with a clean room arrangement enclosing the aseptic bottling or container filling plant and a filter unit for filtering air entering the clean room, and a method of operation thereof.

20 Claims, 5 Drawing Sheets

(56) References Cited

U.S. PATENT DOCUMENTS

| | | | |
|---|---|---|---|
| 6,849,100 B2* | 2/2005 | Lim et al. | 55/385.2 |
| 7,083,663 B2* | 8/2006 | Shih et al. | 95/283 |
| 7,175,699 B2* | 2/2007 | Aubert | 96/224 |
| 7,267,710 B2* | 9/2007 | Tatsuhara et al. | 95/133 |
| 7,655,080 B2* | 2/2010 | Ting | 96/225 |
| 7,896,947 B2* | 3/2011 | Takahashi et al. | 95/26 |
| 2003/0164091 A1* | 9/2003 | Hill et al. | 95/90 |
| 2008/0083337 A1* | 4/2008 | Yamanaka et al. | 96/222 |

FOREIGN PATENT DOCUMENTS

| | | |
|---|---|---|
| DE | 94 00 480 | 5/1994 |
| DE | 101 56 696 | 6/2003 |
| DE | 697 18 712 | 10/2003 |
| EP | 0 815 919 | 1/1998 |
| JP | 62-061614 A | 3/1987 |
| JP | 62-293034 A | 12/1987 |
| JP | 63077614 U | 5/1988 |
| JP | 63 274426 | 11/1988 |
| JP | 1228519 A | 9/1989 |
| JP | 08 021642 | 1/1996 |
| JP | 10-015326 A | 1/1998 |
| JP | 10-016925 A | 1/1998 |
| JP | 11-105832 A | 4/1999 |
| JP | 2006-014848 | 1/2006 |
| JP | 2006-142262 A | 6/2006 |
| WO | WO 2008/001471 | 1/2008 |

OTHER PUBLICATIONS

International Search Report PCT/EP2007/006806 and English translation thereof.
English abstract of JP-09-122424-A.

* cited by examiner

ASEPTIC BOTTLING OR CONTAINER FILLING PLANT WITH A CLEAN ROOM ARRANGEMENT ENCLOSING THE ASEPTIC BOTTLING OR CONTAINER FILLING PLANT AND A FILTER UNIT FOR FILTERING AIR ENTERING THE CLEAN ROOM, AND A METHOD OF OPERATION THEREOF

CONTINUING APPLICATION DATA

This application is a Continuation-In-Part application of International Patent Application No. PCT/EP2007/006806, filed on Aug. 1, 2007, which claims priority from Federal Republic of Germany Patent Application No. 10 2006 036 476.7, filed on Aug. 4, 2006. International Patent Application No. PCT/EP2007/006806 was pending as of the filing date of this application. The United States was an elected state in International Patent Application No. PCT/EP2007/006806.

BACKGROUND

1. Technical Field

The present application relates to an aseptic bottling or container filling plant with a clean room arrangement enclosing the aseptic bottling or container filling plant and a filter unit for filtering air entering the clean room, and a method of operation thereof. This present application also relates to a filter unit for cleaning air with at least one filter layer and a method for the sterilization of such a filter unit.

2. Background Information

Background information is for informational purposes only and does not necessarily admit that subsequently mentioned information and publications are prior art.

A beverage bottling plant for filling bottles with a liquid beverage filling material can possibly comprise a beverage filling machine with a plurality of beverage filling positions, each beverage filling position having a beverage filling device for filling bottles with liquid beverage filling material. The filling devices may have an apparatus designed to introduce a predetermined volume of liquid beverage filling material into the interior of bottles to a substantially predetermined level of liquid beverage filling material. The apparatus designed to introduce a predetermined flow of liquid beverage filling material further comprises an apparatus that is designed to terminate the filling of the beverage bottles upon the liquid beverage filling material reaching the predetermined level in bottles. There may also be provided a conveyer arrangement that is designed to move bottles, for example, from an inspecting machine to the filling machine. Upon filling, a closing station closes the filled bottles. There may further be provided a conveyer arrangement configured to transfer filled bottles from the filling machine to the closing station. Bottles may be labeled in a labeling station, the labeling station having a conveyer arrangement to receive bottles and to output bottles. The closing station and the labeling station may be connected by a corresponding conveyer arrangement.

Container handling machines include, for example, filling machines, capping machines, rinsers etc. In higher-capacity bottling plants, these machines employ a rotating construction, whereby the handling spaces that hold the containers are located on the periphery of a carousel and carry along the containers in a circulating movement during handling operations.

In some plants, the product with which a bottle or container is to be filled is a hygienically and/or microbiologically sensitive product, such as wine, beer, carbonated fruit-flavored beverages, milk products, juices, or pharmaceutical or medicinal products. Such products may be dispensed in bottles or similar containers aseptically, i.e. under clean room conditions, which bottles or containers are then closed aseptically under clean room conditions.

Some plants for aseptic bottling have a clean room or clean room area inside an enclosure which is closed off from the outside and is supplied with filtered, sterile air, and through which a conveyor line for the containers or bottles runs. In a plant of this type, inside the clean room area, a rinser, a filling machine and a capper can be provided one after another in the direction of transport. This clean room area may also be surrounded by a security area in which there are, among other things, air locks or pass-throughs for the feed of the empty containers to be filled and for the removal of the filled and capped containers. In order to maintain the desired level of cleanliness in the clean room, air filtration units may be used to remove contaminants from the air as it enters or travels through the clean room.

Filter units for cleaning air are known in a wide variety of configurations. HEPA filters are used in cases in which a high filtering capability, for example with regard to the removal of particles 0.1 μm and larger, is required and/or desired. These filters can be used to remove, restrict and/or minimize suspended substances and other particulates in the air to be filtered across a wide range of sizes, whereby there are configurations that remove 99.999% of the particulates 0.1 μm and larger from the ambient air. A filter capacity of this type is required or desired for the generation and maintenance of clean room conditions, either for chip production, in surgical theaters, or in aseptic plants for the treatment of containers, such as bottles or cans, for example, or for the filling of such containers.

In the last two applications or uses mentioned in the preceding paragraph, an aseptic atmosphere should be maintained, i.e. harmful microorganisms, spores, etc., should be removed as completely as possible from the ambient air, whereby it may be useful if such substances have already been removed from the incoming air by filtering.

Under some conditions it may be necessary or desired to sterilize or clean such filters, for example to maintain their filtering capacity or for repair or maintenance work.

Various methods are used for the sterilization of such filters, including treatment with chemical disinfectants or irradiation with UV light. Hydrogen peroxide or formaldehyde, for example, can be used for chemical disinfection.

Some sterilization methods for such filter systems have a series of disadvantages. Many chemical disinfectants, such as formaldehyde, for example, have a foul odor, are carcinogens or are otherwise harmful to health, which makes their use complicated, expensive and risky. For irradiation with UV light, complex and expensive irradiation devices are required and/or desired. When external irradiation devices are used, the filter elements must or should be removed, restricted, and/or minimized from their housing in an unsterilized condition, which can be a hazardous operation depending on the filter residues in the filters. During these operations, the filter must or should also be taken out of operation. The integration of the corresponding irradiation devices is frequently economically unacceptable.

OBJECT OR OBJECTS

An object of the present application is to make available a filter unit and a method for the sterilization of such a filter unit which makes possible a safe and successful sterilization of the filter and can simultaneously or substantially simultaneously be carried out at an economically reasonable cost.

SUMMARY

The present application teaches that this object can be accomplished by a filter unit for cleaning air with at least one filter layer, wherein in the filter unit, there is also a heater device for heating the air, and by a method for the sterilization of such a filter unit wherein a sterilization medium in vapor and/or liquid form is introduced into the filter unit and/or into the at least one filter layer. The sterilization medium is activated by means of a gaseous medium at a temperature above an activation temperature of the sterilization medium, whereby the gaseous medium is heated by means of the heater device located inside the filter unit.

In the method according to the present application, the actual filter sterilization takes place by means of a vapor or liquid sterilization medium which can be activated by adding a specified quantity of heat T which heats it above an activation temperature. The sterilization medium is in one possible embodiment hydrogen peroxide ($H_2O_2$).

For this purpose, the sterilization medium is introduced into the filter unit or, depending on its construction, into or onto the filter layers, and is then heated above its activation temperature by feeding in hot air. In this manner a decomposition reaction is initiated during which, among other things, free radicals are formed, which in addition to other reactions kill microorganisms, germs, etc., that are present inside the filter. Upon completion of the reaction, what remains is essentially water and a few decomposition products.

In the filter unit according to the present application, a heating device is provided to heat the air to be filtered. This heating device makes it possible to heat the air directly in the filter unit to the temperature required or desired for activation, which makes possible a surprisingly simple and economical construction.

By means of such filter units with an integrated heating device, various degrees in process control can be achieved in plants equipped with such filter units. For example, in addition to the simple sterilization of the filter itself described above, tempered, filtered air can be fed directly and simply to the plant. As a result of the integration of electrically heated heating elements, for example, the temperature can be controlled easily. Complicated and expensive additional heating device in the interior of the clean rooms or external heating devices with transport temperature losses are no longer necessary or desire. The heating elements are located outside the clean rooms, which greatly simplifies the maintenance, repair or replacement of such elements, because access to the interior of the clean room is no longer necessary or desired.

Filter elements of this type can also be used to support sterilization processes in the interior of the clean room, if they are sterilized with a process similar to the one used to sterilize the filter itself, i.e. by using $H_2O_2$, for example. In this case the interior of the clean room is supplied with a sufficient quantity of liquid and/or vapor sterilization medium, which is activated by the introduction of a sufficient quantity of heated air which, as described above, can be produced easily and precisely or generally by the filter units according to the present application, so that the reaction also takes place in the interior of the clean room.

These and additional configurations of the present application are described below and are an object of the present application.

The above-discussed embodiments of the present invention will be described further herein below. When the word "invention" or "embodiment of the invention" is used in this specification, the word "invention" or "embodiment of the invention" includes "inventions" or "embodiments of the invention", that is the plural of "invention" or "embodiment of the invention". By stating "invention" or "embodiment of the invention", the Applicant does not in any way admit that the present application does not include more than one patentably and non-obviously distinct invention, and maintains that this application may include more than one patentably and non-obviously distinct invention. The Applicant hereby asserts that the disclosure of this application may include more than one invention, and, in the event that there is more than one invention, that these inventions may be patentable and non-obvious one with respect to the other.

BRIEF DESCRIPTION OF THE DRAWINGS

Additional embodiments of the present application are presented in the accompanying drawings.

DESCRIPTION OF EMBODIMENT OR EMBODIMENTS

Figure 1:
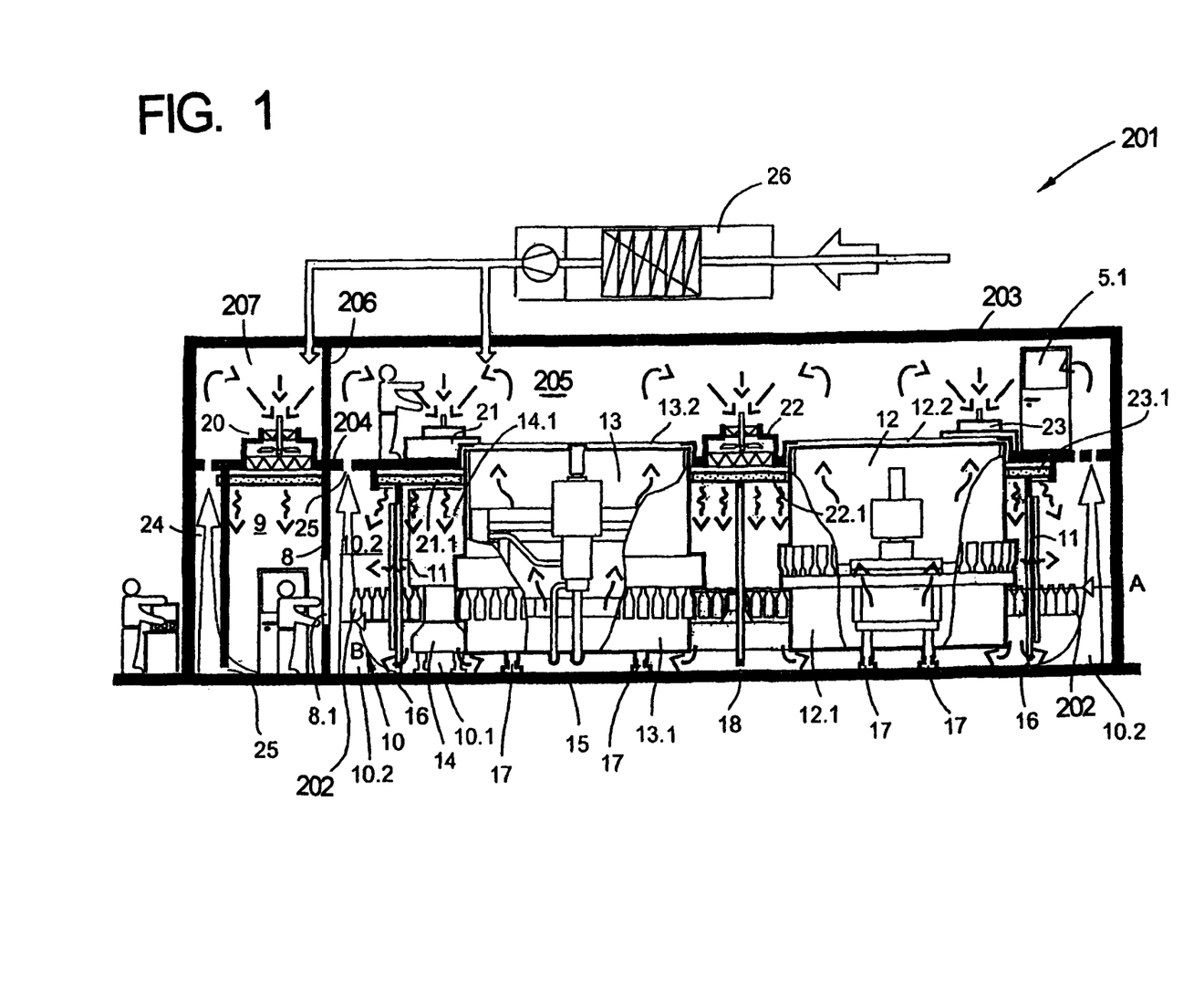
FIG. 1 is a simplified view in elevation of a plant as claimed by the present application for the aseptic bottling of a liquid in bottles or similar containers.
Figure 2:
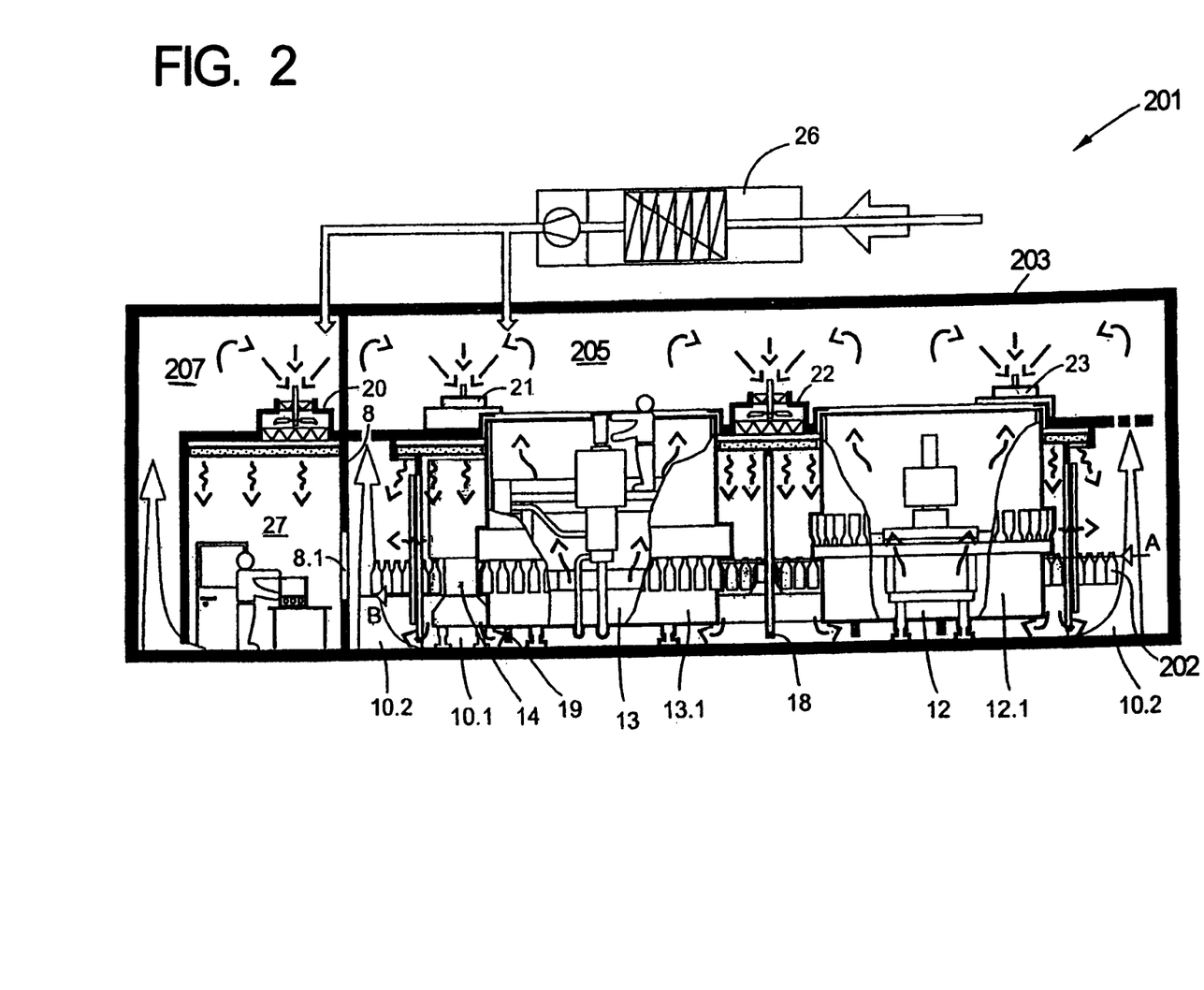
FIG. 2 is a simplified view in elevation of the plant illustrated in FIG. 1, but in a different sectional plane.
Figure 3:
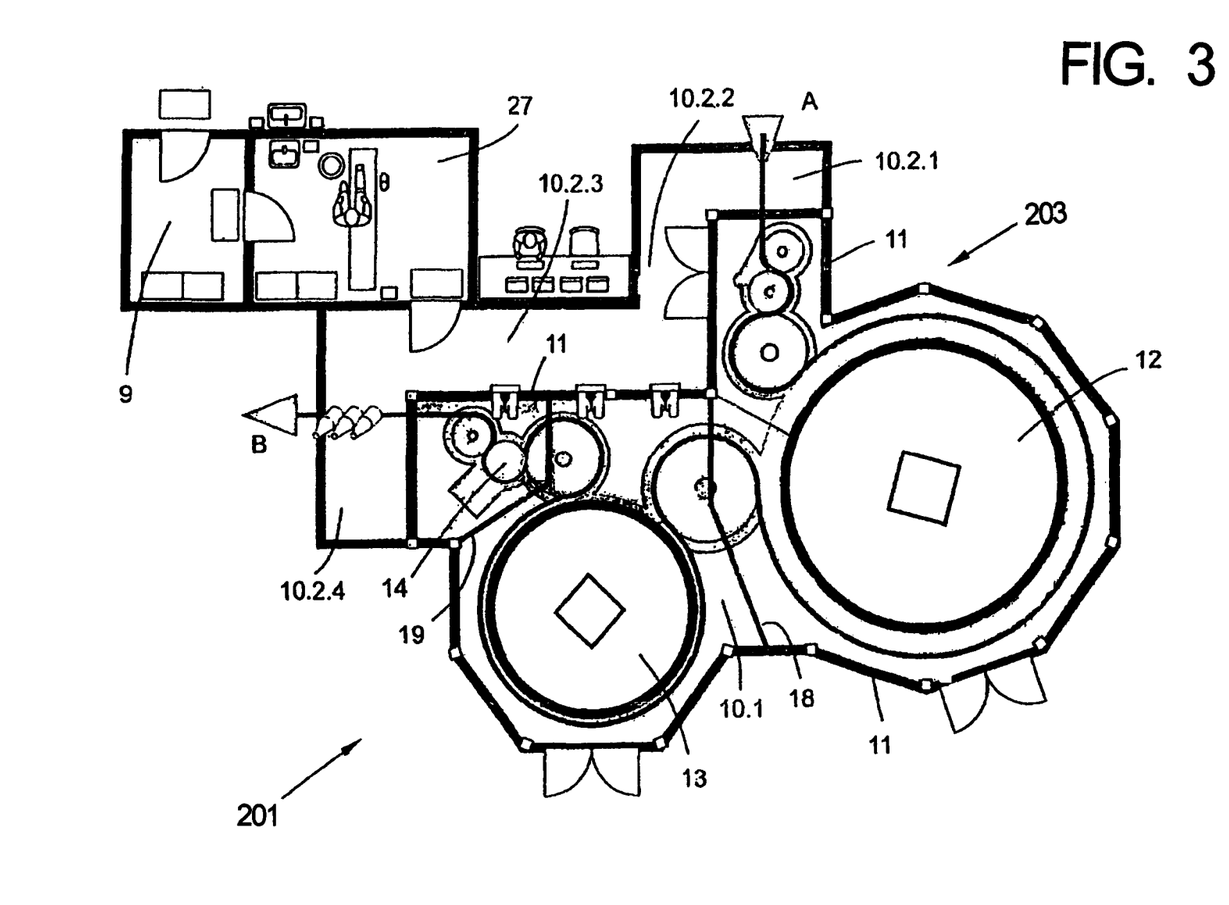
FIG. 3 is a horizontal projection of a plant for the aseptic bottling that is similar to the plant illustrated in FIG. 1.

The plant designated 201 in general in FIGS. 1-3 is used for the aseptic bottling of a liquid in containers or bottles under clean room conditions, for example of a sensitive and/or highly perishable liquid such as a milk product, fruit juice or similar product, for example, or for the bottling of pharmaceutical products.

Please note that reference numeral 204 is referred to as both a "false floor" and a "false ceiling." To clarify, reference numeral 204 is referred to as a "false floor" when the upper portion of the below described bottling plant is being referred to, that is, when reference numeral 204 acts essentially as a floor. In contrast, reference numeral 204 is referred to as a "false ceiling" when the lower portion of the below described bottling plant is being referred to, that is, when reference numeral 204 acts essentially as a ceiling.

The plant 201 comprises essentially an outer housing 203 which encloses an interior which is essentially tightly closed from the exterior, and which is divided into an upper area and a lower area by an accessible false floor 204 (false ceiling). The upper area forms, over the larger portion of the horizontal projection in FIG. 1, a plenum 205 (ceiling space or intermediate room) with access door 5.1 and an auxiliary room 207 which is separated from said plenum 205 by a vertical partition 206. Both the plenum 205 and the auxiliary room 207 are tall enough that said rooms can be entered by persons standing upright, e.g. to perform repair or maintenance work.

The space below the false floor 204 is divided by vertical walls 8 with sealed windows 8.1 into, among other things, a personnel entry airlock 9 and a sterile space 10, which in the plant illustrated in FIG. 1 is located below the plenum 205. For its part, the sterile room 10 is in turn divided by a partition or insulating wall 11 that encloses the machines used in the plant 201 into an inner clean room area 10.1 and an outer security area 10.2.

The partition or insulating wall 11 is realized, at least in part, in the form of a glass wall, so that the machines that are installed in the clean room segment 10.1 are visible from the security area 10.2, and thus the proper operation of these machines, among other things, can be observed.

In the illustrated embodiment, in the clean room area 10.1 there are a rinser 12 which, among other things, sterilizes the bottles 202 that have already been cleaned, a filling machine 13 to fill the sterilized bottles 202 with the liquid to be bottled, a capper 14 to close the bottles and transport devices to transport the bottles 202 between the rinser 12, the filling machine 13 and the capper 14. The rinser 12, the filling machine 13 and the capper 14 are all machines with a rotary design and a rotating rotor.

The empty bottles 202 are fed in the direction indicated by the Arrow A in FIGS. 1-3 by means of a conveyor over the security area 10.2 and through an opening or lock in the wall 11 to the rinser 12. The filled and capped bottles are transported away in the direction indicated by the Arrow B in FIGS. 1-3 by means of the conveyor through an opening or airlock in the wall 11, first into the security area 10.2 and from there out of the housing 203.

The wall 11 hermetically seals the clean room area 10.1, including the vicinity of the underside of the false floor 204, off from the security area. In the vicinity of the floor 15, there are openings 16 in the wall 11 for the passage of air from the clean room area 10.1 into the security area 10.2.

The rinser 12 and the filling machine 13 each have a shield wall or cylindrical shield 12.1 or 13.1 that enclose the respective machine and/or its rotor. These shields are each essentially in the shape of a hollow cylinder that lies with its axis equi-axial with the vertical machine axis and is open on the bottom and top of the machine. Because the machines generally stand on the floor 15 with feet 17, the lower edge or the bottom opening of each shield 12.1 or 13.1 is at some distance from the floor 15, so that between the floor and the lower edge of each shield 12.1 and 13.1 there is a ring-shaped opening for the entry of air from the space surrounding the respective machine into the interior of the shield 12.1 or 13.1. In the vicinity of the upper end, the shields 12.1 and 13.1 are connected in a sealed manner through the false floor 204, where they are covered by a grid or screen 12.2 or 13.2, for example, so that although air can flow out of the interior of the respective cover 12.1 or 13.1 into the plenum 205, the false floor 204 is still accessible in the area of the shields 12.1 and 13.1.

In one possible embodiment, the cylindrical shields 12.1 and 13.1 can extend all the way to, and possibly beyond, the false ceiling 204. Such a design essentially encloses the annular space above the rinser and the filling machine, thus minimizing the space of the clean room where sterile air is continuously introduced or flows. Further, the cylindrical shields 12.1 and 13.1 minimize or substantially reduce the size of the clean room area where sterile air is continuously introduced or flows. Without the shields 12.1 and 13.1, sterile air would occupy a substantially larger area of the clean room, which would result in more work from the filters 21, 22, and 23 and the distribution ducts 21.1, 22.1, and 23.1. A smaller area to fill with sterile air would result in lower energy use, lower costs, and less wear and tear on the filters and distribution ducts, possibly resulting in fewer repairs and less maintenance work.

The extension of the cylindrical shields 12.1 and 13.1 to or beyond the false ceiling 204 permits access to the machines inside the shields for maintenance or repair purposes. Further, since the cylindrical shields 12.1 and 13.1 sit off the floor and create a ring-shaped space around their respective machines, sterile air is permitted to flow from the clean room area surrounding the shields 12.1 and 13.1, through the ring-shaped space. The air then moves upward into the inside of the shields, then out through vents in the false ceiling 204. This upward flow of sterile air permits repairs or maintenance to be performed to the machines on the inside of the shields 12.1 and 13.1 without contaminating the sterile air in the clean room.

The cylindrical shields 12.1 and 13.1 also protect the sterile air in the clean room area from contaminates which may be generated from the rinser or filling machine. Since the rinser and filling machine operate within the confines of the shields 12.1 and 13.1, and the air inside the shields flows up and out through a vent in the false ceiling 204, most all of the airborne contaminates generated by the machines flow out and away from the sterile environment. The machines are effectively substantially sealed off from the clean room area, and any contaminates produced during the machines' operation are essentially kept from entering the clean room area and contaminating the sterilized air therein.

In the clean room area 10.1 there are additional partitions 18 and 19. The partition 18 is between the rinser 12 and the filling machine 13, and the partition 19 is between the filling machine 13 and the capper 14. In the illustrated embodiment, the partitions each form air passage openings on the floor 15. They also have openings to make possible the transfer of bottles between the individual sections.

In the false floor 204 there are a plurality of filtering devices 20-23 to produce sterile air by filtering. The filtering devices 20-23 are used not only for filtering, but can also be used to heat or cool the air. In addition to a filter and a fan, in such an application there can also be a heating or cooling element that is formed by a heat exchanger.

By means of the filtering device 20, air is sucked out of the auxiliary space 207 and filtered, i.e. it is introduced into the personnel entry airlock 9 in the form of sterile air. In the vicinity of the bottom 15, the personnel entry airlock 9 has an air outlet opening that empties into a vertical air duct 24, by means of which the air can flow out of the personnel entry airlock 9 back into the auxiliary room 207.

With the filter device 21, air is sucked out of the plenum 205 and filtered, i.e. the greater part of it is blown in the form of sterile air into the portion of the clean room area 10.1 that is occupied by the capper 14, and partly also into a hollow cylindrical shield 14.1 of the capper 14, so that the working and capping area of the capper receive a constant flow of with sterile air. A small portion of the filtered sterile air supplied by the filter device 21 gets into the security area 10.2.

From the filtering device 22, air is sucked out of the plenum 205 and introduced filtered in equal parts on both sides of the partition 18, i.e. in the form of sterile air into the portion of the clean room area 10.1 occupied by the rinser 12 and into the area occupied by the filling machine 13. The filtering device 23 also sucks air out of the plenum 205 and introduces it into the portion of the clean room area 10.1 occupied by the rinser 12, and so that at least a portion of the airflow generated by the filtering device 23 flows downward along the inside of the partition 11, and thereby also forms an air curtain at the airlock opening, at which the bottles 202 to be filled are transported in the upright position from the security area 10.2 into the clean room area 10.1 or to the rinser 12. A similar air curtain of filtered and sterile air is also formed at the airlock opening, at which the filled and capped bottles 202 travel out of the clean room area 10.1 into the security area 10.2.

As illustrated by the arrow that represents the airflow, the majority of the airflow generated by the filtering devices 21-23 flows upward via the interior of the shields 12.1 and 13.1 and then returns to the plenum 205 at the top of the respective shield. A portion of the airflow generated by the filtering devices 21-23 also flows through the openings 16 out of the clean room area 10.1 into the security area 10.2 and, like the sterile air from the filtering device 21, is introduced directly into the security area 10.2 and flows back into the plenum 205 via ventilation openings provided in the false floor 204.

In another possible embodiment, a portion of the airflow generated by the filtering devices 21-23 also flows through the openings 16 out of the clean room area 10.1 into the security area 10.2 and, like the sterile air introduced directly into the security area 10.2 by the filtering device 21, flows back into the plenum 205 via at least one ventilation opening provided in the false floor 204.

In the embodiment illustrated, the filtering devices 21, 22 and 23 have distribution ducts 21.1, 22.1 and 23.1 respectively for air distribution on the underside of the false floor 204.

In FIG. 1, 26 is an external air-conditioning unit which, among other things, has a filter stage and an air-conditioning stage, and by means of which the plenum 205 and the auxiliary space 207 are supplied with filtered and air-conditioned fresh air.

The air-conditioning unit 26 as well as the individual filtering devices 20, 21, 22 and 23 are regulated so that the air pressure in the sterile space 10 is in any case higher than atmosphere pressure, and higher than the air pressure in the additional rooms adjacent to the sterile room 10, such as the plenum 205, the auxiliary room 207, the personnel entry airlock 9 etc. The external air-conditioning unit 26 and the filtering devices 20 are also regulated so that the pressure in the plenum 205, in the auxiliary room 207 and in the personnel entry airlock 9 and in the rooms adjacent to them is above the atmospheric pressure outside the housing 203. The air-conditioning unit 26 compensates for the air losses that occur on account of, among other things, the openings for the introduction and removal of containers and caps into and from the clean room.

The plant 201 is designed so that in the clean room 10.1, Clean Room Class 100 (approximately 3,500 particles per m³ of air) is achieved. The sterile space 10 itself has a relatively small volume, which significantly reduces, among other things, the costs for air conditioning and air treatment. Also, in the event of any operational interruptions, the interiors of the shields 12.1 and 13.2 are accessible, i.e. repair and maintenance interventions can be carried out on the rinser 12 and on the filling machine 13, and namely via the upper cover 12.2 or 13.2 from the plenum 205. Because of the routing of the airflow out of the areas surrounding the rinser 12 and the filling machine 13 upward through the shields 12.1 and 13.1, in the space 10 outside the shields, i.e. in the sterile area itself, the conditions of Clean Room Class 100 can be maintained even during repairs and maintenance operations on the rinser 12 and on the filling machine 13.

FIG. 2 shows the plant illustrated in FIG. 1 in a modified view in elevation. This figure also shows a working or waiting room 27 for the operating personnel. This room 27, which is also supplied with filtered, sterile air via a filtering device 20 from the auxiliary space 207, is accessible via the personnel entry airlock 9. The room 10 can be reached if necessary from the room 27 or via a corresponding door. In the partition 8 which also separates the room 27 from the room 10, there is also at least one view window 8.1.

FIG. 3 shows, in a somewhat modified form, the horizontal projection of the plant 1a. The security area 10.2 does not completely enclose the clean room area 10.1, but this security area 10.2 is adjacent only to a smaller part of the periphery of the clean room area 10.1, i.e. the wall 11 that encloses the clean room area 10.2 not only forms a partition between the security area 10.2 and the clean room area 10.1, but over the greater part of its length directly seals the clean room area 10.1 off from the environment. This configuration makes a significant contribution to minimize the volume of the space that is to be supplied with sterile and controlled-temperature air, which in turns minimizes operating costs.

As shown in FIG. 3, in this realization the secure area 10.2 has a horizontal projection that comprises a plurality of Z or zig-zag shapes and comprises a plurality of segments 10.2.1-10.2.4, each of which is adjacent to another at right angles, whereby the inlet for the bottles 202 is provided in the segment 10.2.1 and the outlet for the filled bottles is provided in the segment 10.2.4, and the conveyor devices (Arrows A and B) for the bottles 202 run at a right angle to each other at the inlet and the outlet.

FIG. 3 further shows the relation of the wall 11 to the cylindrical shields 12.1 and 13.1. In this embodiment, the wall 11 essentially substantially outlines the outer edges of the shields 12.1 and 13.1 of the rinser 12 and the filling machine 13 in order to reduce the amount of open space in the clean room area 10.1. The wall 11 essentially forms a substantially polygonal shape around the outer edges of the shields 12.1 and 13.1. Please note that any number of sides may possibly be used to form the essentially polygonal outline of the shields 12.1 and 13.1. Further, the wall 11 may be rounded around the edges of the shields 12.1 and 13.1 instead of having a polygonal shape. The embodiment of the wall 11 in FIG. 3 is not meant to limit the shape of the wall 11 in any way, as other shapes and embodiments of the wall 11 are possible.

Figure 4:
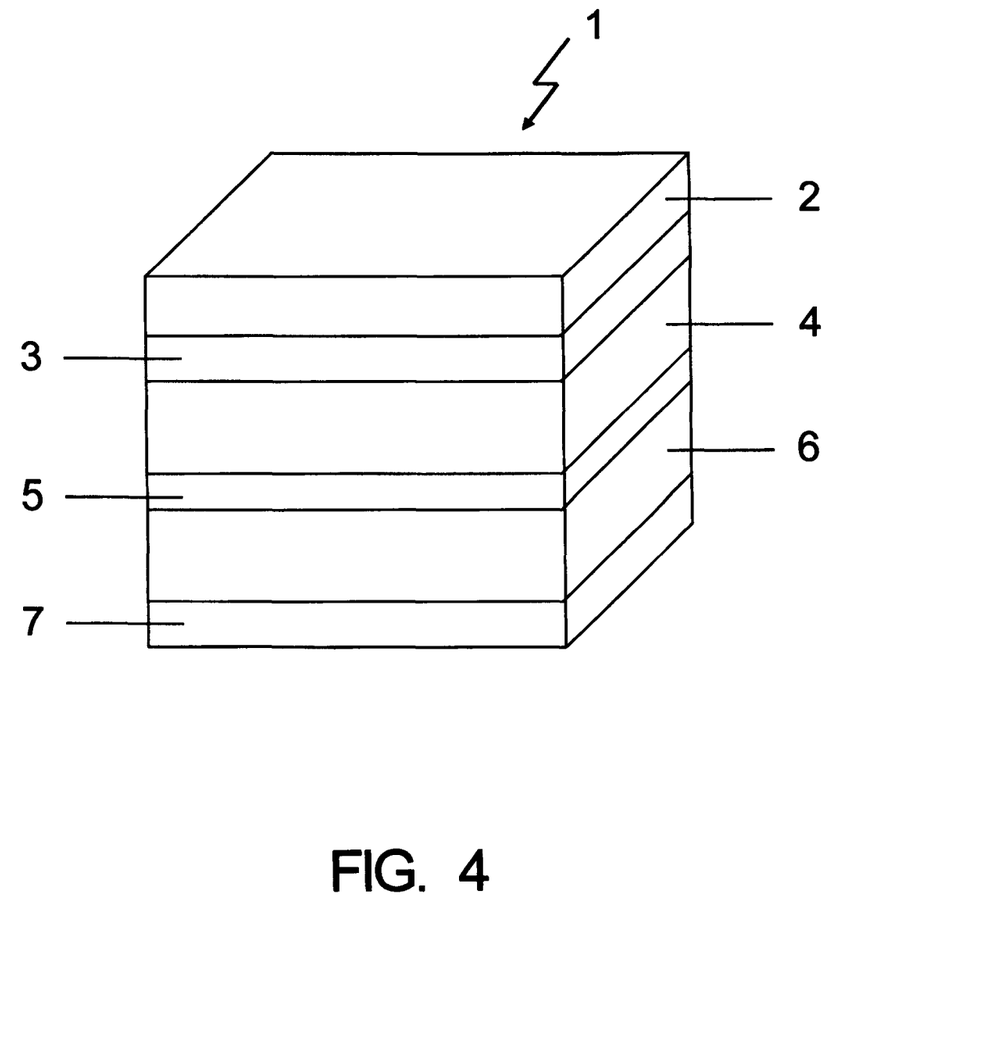
FIG. 4 shows a schematic three-dimensional view of a filter unit according to the present application.

FIG. 4 discloses a filter unit 1 for purifying air with a stacked construction that presents a large surface area. It is to be located in a housing which is not illustrated in any further detail, and is provided with air inlets and outlets, or is fastened with its underside to a clean room to be supplied with air.

Located on the air supply side of the filter unit 1 is an upstream rough filter layer 2 which is used to remove large particulates and impurities from the air that is sucked in, to ease the burden on the actual filter layers which are located behind it. Located underneath it is a controllable fan 3 which provides the desired air flow through the filter unit 1. Alternatively, the blower can also be located outside the filter unit 1.

The next item connected in the series is an electrical heating device 4.

This electrical heating device 4 can be constructed using the conventional lamellar construction and has a nominal heating output appropriate to the filter capacity of the unit. For one possible embodiment having a filter capacity of fifteen hundred cubic meters per hour (approximately nine hundred cubic feet per minute (cfm)) and a heating of the airflow to eighty degrees Celsius, a heating capacity of the heating device 4 of approximately thirty-six kilowatts may be utilized.

Some examples of filters having a filter capacity of at least nine hundred cubic feet per minute (cfm) are the Filtra 2000 (™) line of filters available from Camfil Farr, Inc., One North Corporate Drive, Riverdale, N.J. 07457. The following table lists the specifications for different filters in the Filtra 2000

(TM) line, as published in the Filtra 2000 (™) Product Sheet No. 1823-0606, which document is incorporated by reference:

| Model | Efficiency | Nominal Size | Airflow (cfm) | Resistance @ Airflow | Media Area |
|---|---|---|---|---|---|
| FA 1565-03-01 | 95% | 24 × 12 × 11.50 | 900 | 0.50 | 174 |
| FA 1563-03-01 | @ 0.3 | 24 × 24 × 11.50 | 1500 | | 237 |
| FA 1561-03-01 | Micron | 24 × 24 × 11.50 | 2000 | | 390 |
| FA 1560-03-01 | | 24 × 24 × 11.50 | 2400 | | 431 |
| FA 1565-01-01 | 99.99% | 24 × 12 × 11.50 | 900 | 1.0 | 174 |
| FA 1563-01-01 | @ 0.3 | 24 × 24 × 11.50 | 1500 | | 237 |
| FA 1561-01-01 | Micron | 24 × 24 × 11.50 | 2000 | | 390 |
| FA 1560-01-01 | | 24 × 24 × 11.50 | 2400 | | 431 |
| FA 1565-02-01 | 99.999% | 24 × 12 × 11.50 | 693 | 1.0 | 174 |
| FA 1563-02-01 | @ 0.3 | 24 × 24 × 11.50 | 1155 | | 237 |
| FA 1561-02-01 | Micron | 24 × 24 × 11.50 | 1540 | | 390 |
| FA 1560-02-01 | | 24 × 24 × 11.50 | 1848 | | 431 |

These models have a maximum operating temperature of approximately one hundred and seventy-five degrees Fahrenheit or eighty degrees Celsius if used without a gasket, and have a maximum operating temperature of approximately two hundred degrees Fahrenheit or ninety degrees Celsius if used with a neoprene gasket.

Downstream of the heating device 4 is a first HEPA (High Efficiency Particulate Air) filter layer 5 and, depending on the application, a ULPA (Ultra Low Particulate Air) filter layer, e.g. in Class U16, which makes possible the actual filtering of particulates, microorganisms, etc. Downstream of that is a sterilization layer 6, by means of which liquid or vapor $H_2O_2$ can be introduced into the filter layer 5. Downstream of the sterilization layer 6 is an additional HEPA or ULPA filter layer 7, which can also be supplied by the sterilization layer 6 with $H_2O_2$ in liquid or vapor form. In one configuration of the present application it is also possible to use one of the two filter layers 5 or 7 or to connect additional filter layers to them.

In normal operation, the required and/or desired stream of fresh air is sucked in by the controllable fan 3, is heated by the adjustable heater device 4 to the required or desired temperature and is then cleaned by the filter layers 5 and 7, so that at the output of the filter a high-purity air flow is available in the connected room which, depending on the configuration of the filter layers, is up to 99.9% free of dust particles or microorganisms larger than 0.1 to 0.3 μm, or as a result of the use of even more efficient ULPA filter layers is up to 99.999% free of the above mentioned parties, viruses, bacteria, mite eggs and precipitates, pollen, etc.

For example, if the filter itself is to be sterilized in a regular sterilization cycle or to perform unscheduled maintenance, these operations can be carried out with the method according to the present application as follows:

First, $H_2O_2$ in liquid or vapor form is introduced into the two filter layers 5 and 7 in sufficient quantity. For this purpose, the fan 3 can be temporarily deactivated. When a sufficient saturation of $H_2O_2$ in the filter layers has been achieved, the heater device 4 is activated and the fan 3 is used to direct hot air through the filter layers that comprise the $H_2O_2$. Consequently the sterilization medium is heated above its activation temperature so that a decay process begins in which free radicals are formed, among other intermediate products, which essentially ensure and/or promote a decomposition of any microorganisms, etc., it may comprise. After the completion of the reaction, after the activation of the fan 3, for the duration of which, after the activation, the fan 3 can be turned off again, the remaining reaction products are essentially water and a few decomposition residues. By means of the activation of the fan 3, optionally in combination with the activation of the heater device 4, the filter layers 5 and 7 can then be dried and the excess decomposition products can be blown out.

Alternatively, the fan 3 can also be operated in the opposite direction of airflow to keep from overloading the connected clean room. This measure is unnecessary or undesired if the filter sterilization is performed in the context of a sterilization cycle together with the adjacent clean room.

Figure 5:
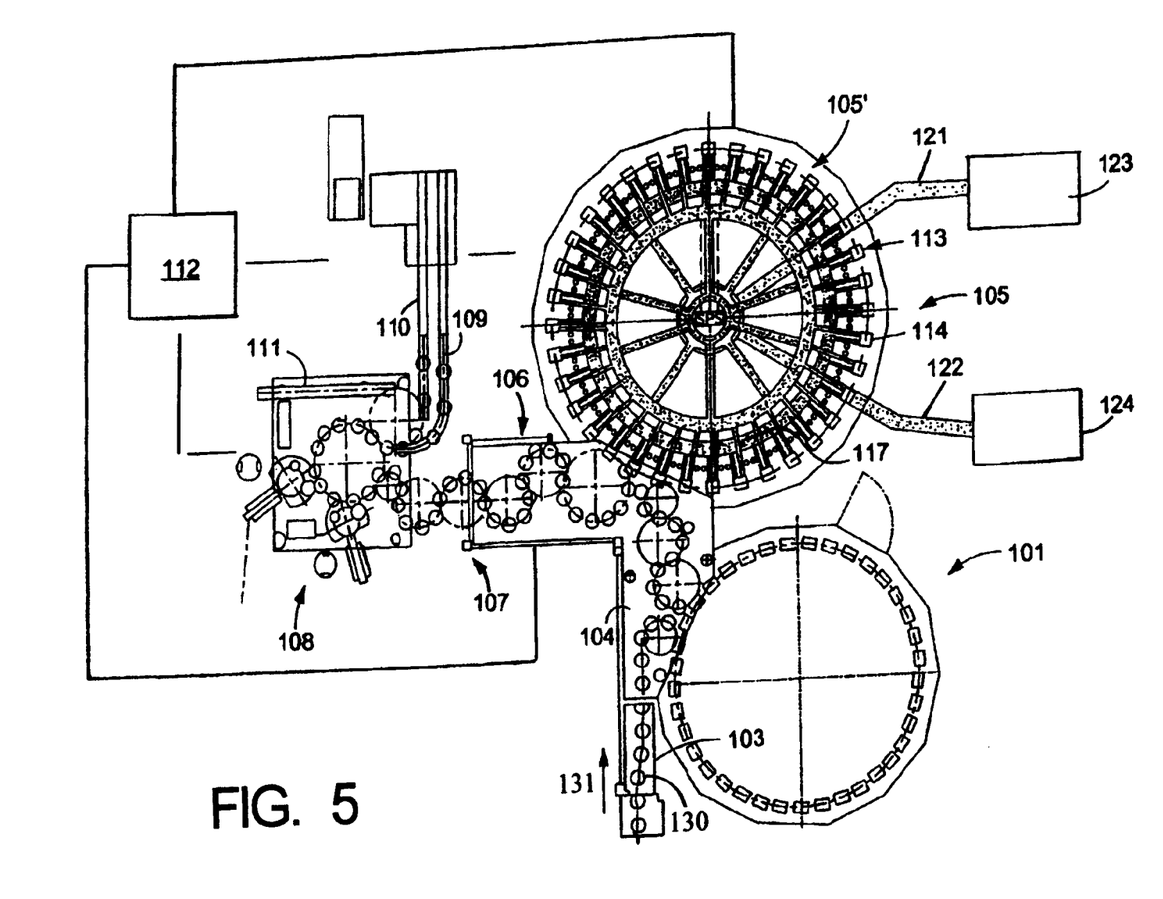
FIG. 5 shows schematically the main components of one possible embodiment example of a system for filling containers.

FIG. 5 shows schematically the main components of one possible embodiment example of a system for filling containers, specifically, a beverage bottling plant for filling bottles 130 with at least one liquid beverage, in accordance with at least one possible embodiment, in which system or plant could possibly be utilized at least one aspect, or several aspects, of the embodiments disclosed herein.

FIG. 5 shows a rinsing arrangement or rinsing station 101, to which the containers, namely bottles 130, are fed in the direction of travel as indicated by the arrow 131, by a first conveyer arrangement 103, which can be a linear conveyor or a combination of a linear conveyor and a starwheel. Downstream of the rinsing arrangement or rinsing station 101, in the direction of travel as indicated by the arrow 131, the rinsed bottles 130 are transported to a beverage filling machine 105 by a second conveyer arrangement 104 that is formed, for example, by one or more starwheels that introduce bottles 130 into the beverage filling machine 105.

The beverage filling machine 105 shown is of a revolving or rotary design, with a rotor 105', which revolves around a central, vertical machine axis. The rotor 105' is designed to receive and hold the bottles 130 for filling at a plurality of filling positions 113 located about the periphery of the rotor 105'. At each of the filling positions 103 is located a filling arrangement 114 having at least one filling device, element, apparatus, or valve. The filling arrangements 114 are designed to introduce a predetermined volume or amount of liquid beverage into the interior of the bottles 130 to a predetermined or desired level.

The filling arrangements 114 receive the liquid beverage material from a toroidal or annular vessel 117, in which a supply of liquid beverage material is stored under pressure by a gas. The toroidal vessel 117 is a component, for example, of the revolving rotor 105'. The toroidal vessel 117 can be connected by means of a rotary coupling or a coupling that permits rotation. The toroidal vessel 117 is also connected to at least one external reservoir or supply of liquid beverage material by a conduit or supply line. In the embodiment shown in FIG. 5, there are two external supply reservoirs 123 and 124, each of which is configured to store either the same liquid beverage product or different products. These reservoirs 123, 124 are connected to the toroidal or annular vessel 117 by corresponding supply lines, conduits, or arrangements 121 and 122. The external supply reservoirs 123, 124 could be in the form of simple storage tanks, or in the form of liquid beverage product mixers, in at least one possible embodiment.

As well as the more typical filling machines having one toroidal vessel, it is possible that in at least one possible embodiment there could be a second toroidal or annular vessel which contains a second product. In this case, each filling arrangement 114 could be connected by separate connections to each of the two toroidal vessels and have two individually-controllable fluid or control valves, so that in each bottle 130, the first product or the second product can be filled by means of an appropriate control of the filling product or fluid valves.

Downstream of the beverage filling machine 105, in the direction of travel of the bottles 130, there can be a beverage bottle closing arrangement or closing station 106 which closes or caps the bottles 130. The beverage bottle closing arrangement or closing station 106 can be connected by a third conveyer arrangement 107 to a beverage bottle labeling arrangement or labeling station 108. The third conveyer arrangement may be formed, for example, by a plurality of starwheels, or may also include a linear conveyor device.

In the illustrated embodiment, the beverage bottle labeling arrangement or labeling station 108 has at least one labeling unit, device, or module, for applying labels to bottles 130. In the embodiment shown, the labeling arrangement 108 is connected by a starwheel conveyer structure to three output conveyer arrangements: a first output conveyer arrangement 109, a second output conveyer arrangement 110, and a third output conveyer arrangement 111, all of which convey filled, closed, and labeled bottles 130 to different locations.

The first output conveyer arrangement 109, in the embodiment shown, is designed to convey bottles 130 that are filled with a first type of liquid beverage supplied by, for example, the supply reservoir 123. The second output conveyer arrangement 110, in the embodiment shown, is designed to convey bottles 130 that are filled with a second type of liquid beverage supplied by, for example, the supply reservoir 124. The third output conveyer arrangement 111, in the embodiment shown, is designed to convey incorrectly labeled bottles 130. To further explain, the labeling arrangement 108 can comprise at least one beverage bottle inspection or monitoring device that inspects or monitors the location of labels on the bottles 130 to determine if the labels have been correctly placed or aligned on the bottles 130. The third output conveyer arrangement 111 removes any bottles 130 which have been incorrectly labeled as determined by the inspecting device.

The beverage bottling plant can be controlled by a central control arrangement 112, which could be, for example, computerized control system that monitors and controls the operation of the various stations and mechanisms of the beverage bottling plant.

The present application is not limited to the possible embodiments described above. Numerous variations and modifications can be introduced without going beyond the basic teaching of the present application. For example, the filter geometry is not limited to the stacked construction described above, but can also be used on cylindrical filter arrangements or radial filters, in which the filter layers are oriented coaxially with one another. The number and arrangement of the filter layers can also be modified, depending on the individual requirements, whereby it is not necessary or may not be desired to make all or substantially all or most of the filters sterilizable. In addition to $H_2O_2$, under some conditions, other thermally activated liquid and/or vapor sterilization mediums can be used.

The present application relates to a method for the sterilization of a filter unit 1 and a filter unit 1 for the cleaning of air with at least one filter layer 5, 7 which makes possible a safe, reliable and successful sterilization of the filter and can simultaneously or substantially simultaneously be manufactured economically.

The present application teaches that a sterilization medium in vapor and/or liquid form is introduced into the filter unit 1 and/or into the at least one filter layer 5, 7, and that then the sterilization medium is activated by means of a gaseous medium at a temperature above an activation temperature of the sterilization medium, whereby the gaseous medium is heated by means of a heater device 4 which is provided inside the filter unit.

One feature or aspect of an embodiment is believed at the time of the filing of this patent application to possibly reside broadly in a filter unit for cleaning air with at least one filter layer 5, 7, wherein in the filter unit 1, there is also a heater device 4 for heating the air.

Another feature or aspect of an embodiment is believed at the time of the filing of this patent application to possibly reside broadly in the filter unit, wherein the heater device 4 is provided upstream of the filter layer 5, 7 in the air flow direction.

Yet another feature or aspect of an embodiment is believed at the time of the filing of this patent application to possibly reside broadly in the filter unit, wherein a device 6 is provided for the introduction of a sterilization medium onto and/or into the at least one filter layer 5, 7.

Still another feature or aspect of an embodiment is believed at the time of the filing of this patent application to possibly reside broadly in the filter unit, wherein the sterilization medium is realized in the form of a gaseous medium that can be activated at a temperature above an activation temperature of the sterilization medium.

A further feature or aspect of an embodiment is believed at the time of the filing of this patent application to possibly reside broadly in the filter unit, wherein, to heat the gaseous medium, a heater device 4 is provided inside the filter unit 1.

Another feature or aspect of an embodiment is believed at the time of the filing of this patent application to possibly reside broadly in the filter unit, wherein $H_2O_2$ is provided as the sterilization medium and/or air as the gaseous medium.

Yet another feature or aspect of an embodiment is believed at the time of the filing of this patent application to possibly reside broadly in a method according to the present application, wherein a sterilization medium in vapor and/or liquid form is introduced into the filter unit 1 and/or into the at least one filter layer 5, 7, and that then the sterilization medium is activated by means of a gaseous medium at a temperature above an activation temperature of the sterilization medium, whereby the gaseous medium is heated by means of the heater device 4 located inside the filter unit 1.

Still another feature or aspect of an embodiment is believed at the time of the filing of this patent application to possibly reside broadly in the method, wherein $H_2O_2$ is used as the sterilization medium and/or air as the gaseous medium.

Some examples of HEPA or ULPA filters or filter arrangements that may possibly be utilized or adapted for use in at least one possible embodiment may possibly be found in the following U.S. Pat. No. 7,008,468, entitled "HEPA vacuum recovery system;" U.S. Pat. No. 6,911,061, entitled "In-line HEPA filter;" U.S. Pat. No. 6,619,063, entitled "Indoor air treatment system with HEPA filtration;" U.S. Pat. No. 6,602,128, entitled "Clean air room with a blower including a HEPA filter and ducts;" U.S. Pat. No. 6,428,610, entitled "Hepa filter;" U.S. Pat. No. 6,409,785, entitled "Cleanable HEPA filter media;" U.S. Pat. No. 6,289,974, entitled "Integrated heat recovery ventilator HEPA filter using a HEPA filter material regenerative heat exchanger;" U.S. Pat. No. 6,257,317, entitled "Integrated heat recovery ventilator-hepa filter;" U.S. Pat. No. 6,200,367, entitled "Water washable stainless steel HEPA filter;" U.S. Pat. No. 5,911,332, entitled "HEPA filtered storage canisters;" U.S. Pat. No. 5,814,118, entitled "HEPA filter for venting chambers;" U.S. Pat. No. 5,727,707, entitled "Hepa filtered storage canisters;" U.S. Pat. No. 5,507,847, entitled "ULPA filter;" U.S. Pat. No. 5,358,443, entitled "Dual fan hepa filtration system;" U.S. Pat. No. 5,290,330, entitled "HEPA filtration system;" U.S. Pat. No. 5,288,434, entitled "Hepa filter dissolution process;" U.S. Pat. No. 5,259,854, entitled "Disposable HEPA filtration device;" and U.S. Pat. No. 5,238,477, entitled "Hepa filter unit having a metallic membrane."

The components disclosed in the various publications, disclosed or incorporated by reference herein, may possibly be used in possible embodiments of the present invention, as well as equivalents thereof.

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

The appended drawings in their entirety, including all dimensions, proportions and/or shapes in at least one embodiment of the invention, are accurate and are hereby included by reference into this specification.

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

All, or substantially all, of the components and methods of the various embodiments may be used with at least one embodiment or all of the embodiments, if more than one embodiment is described herein.

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

All of the patents, patent applications and publications recited herein, and in the Declaration attached hereto, are hereby incorporated by reference as if set forth in their entirety herein.

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

It will be understood that the examples of patents, published patent applications, and other documents which are included in this application and which are referred to in paragraphs which state "Some examples of . . . which may possibly be used in at least one possible embodiment of the present application . . . " may possibly not be used or useable in any one or more embodiments of the application.

The sentence immediately above relates to patents, published patent applications and other documents either incorporated by reference or not incorporated by reference.

All of the patents, patent applications or patent publications, which were cited in the International Search Report dated Dec. 19, 2007, and/or cited elsewhere are hereby incorporated by reference as if set forth in their entirety herein as follows: EP 0 815 919, having the title "FILTER UNIT," published on Jan. 7, 1998; JP 63 274426, having the following English translation of the Japanese title "FILTER UNIT," published on Nov. 11, 1988; JP 08 021642, having the following English translation of the German title "DRYING-STERILIZING DEVICE OF FILTER FOR AIR CONDITIONING," published on Jan. 23, 1996; U.S. Pat. No. 4,707,167, having the title "AIR STERILIZATION FILTER," published on Nov. 17, 1987; and DE 26 31 260, having the following German title "VERFAHREN UND VORRICHTUNG ZUM BESEITIGEN VON BAKTERIEN IN DURCH KLIMAANLAGEN ODER DERGLEICHEN AUFBEREITETER LUFT," published on Jan. 19, 1978.

The purpose of incorporating U.S. patents, Foreign patents, publications, etc. is solely to provide additional information relating to technical features of one or more embodiments, which information may not be completely disclosed in the wording in the pages of this application. Words relating to the opinions and judgments of the author and not directly relating to the technical details of the description of the embodiments therein are not incorporated by reference. The words all, always, absolutely, consistently, preferably, guarantee, particularly, constantly, ensure, necessarily, immediately, endlessly, avoid, exactly, continually, expediently, need, must, only, perpetual, precise, perfect, require, requisite, simultaneous, total, unavoidable, and unnecessary, or words substantially equivalent to the above-mentioned words in this sentence, when not used to describe technical features of one or more embodiments, are not considered to be incorporated by reference herein.

The corresponding foreign and international patent publication applications, namely, Federal Republic of Germany Patent Application No. 10 2006 036 476.7, filed on Aug. 4, 2006, having inventor Daryoush SANGI, and DE-OS 10

2006 036 476.7 and DE-PS 10 2006 036 476.7, and International Application No. PCT/EP2007/006806, filed on Aug. 1, 2007, having WIPO Publication No. WO2008/014992 and inventor Daryoush SANGI, are hereby incorporated by reference as if set forth in their entirety herein for the purpose of correcting and explaining any possible misinterpretations of the English translation thereof. In addition, the published equivalents of the above corresponding foreign and international patent publication applications, and other equivalents or corresponding applications, if any, in corresponding cases in the Federal Republic of Germany and elsewhere, and the references and documents cited in any of the documents cited herein, such as the patents, patent applications and publications, are hereby incorporated by reference as if set forth in their entirety herein.

The purpose of incorporating the Foreign equivalent patent application PCT/EP2007/006806 and German Patent Application 10 2006 036 476.7 is solely for the purpose of providing a basis of correction of any wording in the pages of the present application, which may have been mistranslated or misinterpreted by the translator. Words relating to opinions and judgments of the author and not directly relating to the technical details of the description of the embodiments therein are not to be incorporated by reference. The words all, always, absolutely, consistently, preferably, guarantee, particularly, constantly, ensure, necessarily, immediately, endlessly, avoid, exactly, continually, expediently, need, must, only, perpetual, precise, perfect, require, requisite, simultaneous, total, unavoidable, and unnecessary, or words substantially equivalent to the above-mentioned word in this sentence, when not used to describe technical features of one or more embodiments, are not generally considered to be incorporated by reference herein.

Statements made in the original foreign patent applications PCT/EP2007/006806 and DE 10 2006 036 476.7 from which this patent application claims priority which do not have to do with the correction of the translation in this patent application are not to be included in this patent application in the incorporation by reference.

All of the references and documents, cited in any of the documents cited herein, are hereby incorporated by reference as if set forth in their entirety herein. All of the documents cited herein, referred to in the immediately preceding sentence, include all of the patents, patent applications and publications cited anywhere in the present application.

The description of the embodiment or embodiments is believed, at the time of the filing of this patent application, to adequately describe the embodiment or embodiments of this patent application. However, portions of the description of the embodiment or embodiments may not be completely applicable to the claims as originally filed in this patent application, as amended during prosecution of this patent application, and as ultimately allowed in any patent issuing from this patent application. Therefore, any statements made relating to the embodiment or embodiments are not intended to limit the claims in any manner and should not be interpreted as limiting the claims in any manner.

The details in the patents, patent applications and publications may be considered to be incorporable, at applicant's option, into the claims during prosecution as further limitations in the claims to patentably distinguish any amended claims from any applied prior art.

The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the embodiment or embodiments, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

The abstract of the disclosure is submitted herewith as required by 37 C.F.R. §1.72(b). As stated in 37 C.F.R. §1.72 (b):

A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims.

Therefore, any statements made relating to the abstract are not intended to limit the claims in any manner and should not be interpreted as limiting the claims in any manner.

The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

AT LEAST PARTIAL NOMENCLATURE

| 1 | Filter unit |
| --- | --- |
| 2 | Coarse filter layer |
| 3 | Fan |
| 4 | Heater device |
| 5 | First filter layer |
| 6 | Sterilization layer |
| 7 | Second filter layer |

What is claimed is:

1. A method for the sterilization of a self-sterilizing air filter unit, said method comprising:
    activating a fan disposed inside said filter unit and flowing air through said air filter unit;
    temporarily deactivating said fan and then, via a sterilization arrangement disposed inside said filter unit, introducing hydrogen peroxide in vapor and/or liquid form onto and/or into a filter layer disposed inside said filter unit;
    reactivating said fan and flowing air through a heater disposed inside said filter unit; and
    heating the air with said heater to a temperature at or above an activation temperature of the hydrogen peroxide, and thereby activating the hydrogen peroxide to produce free radicals, and thereby destroying microorganisms on or in said filter layer.

2. The method according to claim 1, wherein said step of introducing hydrogen peroxide comprises introducing hydrogen peroxide in vapor and/or liquid form onto and/or into an additional filter layer disposed inside said air filter unit, wherein said sterilization arrangement is disposed between said filter layer and said additional filter layer.

3. The method according to claim 2, wherein said method further comprises deactivating at least one of: said fan and said heater upon completion of activation of the hydrogen peroxide.

4. The method according to claim 3, wherein said method further comprises maintaining operating said fan and deactivating said heater upon completion of activation of the hydrogen peroxide.

5. The method according to claim 4, wherein said method further comprises maintaining operating said fan and reactivating said heater, and thereby evaporating water and blowing out decomposition residues formed by the decomposition of microorganisms by the activated hydrogen peroxide.

6. The method according to claim 3, wherein said method further comprises deactivating said fan and said heater upon completion of activation of the hydrogen peroxide.

7. The method according to claim 6, wherein said method further comprises reactivating said fan, and thereby evaporating water and blowing out decomposition residues formed by the decomposition of microorganisms by the activated hydrogen peroxide.

8. The method according to claim 6, wherein said method further comprises reactivating said fan and said heater, and thereby evaporating water and blowing out decomposition residues formed by the decomposition of microorganisms by the activated hydrogen peroxide.

9. The method according to claim 1, wherein said method comprises filtering up to 99.9% of airborne particles and microorganisms having a size of 0.1 micrometers to 0.3 micrometers from the air flowing through said air filter unit.

10. The method according to claim 1, wherein said method comprises filtering up to 99.999% of airborne particles and microorganisms having a size of 0.1 micrometers to 0.3 micrometers from the air flowing through said air filter unit.

11. The method according to claim 1, wherein said method comprises filtering up to 99.999% of airborne particles and microorganisms having a size of 0.1 micrometers to 0.3 micrometers, viruses, bacteria, mite eggs and precipitates, and pollen, from the air flowing through said air filter unit.

12. A self-sterilizing air filter unit for performing the method according to claim 1, comprising:
a filter layer;
a sterilization arrangement being configured to introduce vapor or liquid hydrogen peroxide onto and/or into said filter layer;
a fan being configured to be activated to flow air through said air filter unit;
a heater being disposed inside said air filter unit upstream of said filter layer, and being configured to heat air passing through said air filter unit to a temperature at or above an activation temperature of hydrogen peroxide; and
said fan being configured to be de-activated upon introduction of vapor or liquid hydrogen peroxide onto and/or into said filter layer, and then re-activated to flow the air heated by said heater through said filter layer to permit activation of the hydrogen peroxide on and/or in said filter layer to produce free radicals and thereby destroy microorganisms on and/or in said filter layer.

13. A self-sterilizing air filter unit comprising:
a filter layer;
a sterilization arrangement being configured to introduce vapor or liquid hydrogen peroxide onto and/or into said filter layer;
a fan being configured to be activated to flow air through said air filter unit;
a heater being disposed inside said air filter unit upstream of said filter layer, and being configured to heat air passing through said air filter unit to a temperature at or above an activation temperature of hydrogen peroxide; and
said fan being configured to be de-activated upon introduction of vapor or liquid hydrogen peroxide onto and/or into said filter layer, and then re-activated to flow the air heated by said heater through said filter layer to permit activation of the hydrogen peroxide on and/or in said filter layer to produce free radicals and thereby destroy microorganisms on and/or in said filter layer.

14. The self-sterilizing air filter unit according to claim 13, wherein said heater is disposed upstream of said filter layer.

15. The self-sterilizing air filter unit according to claim 14, wherein:
said filter layer comprises a first filter layer;
said air filter unit comprises a second filter layer disposed downstream of said first filter layer; and
said sterilization arrangement is disposed between said first filter layer and said second filter layer.

16. The self-sterilizing air filter unit according to claim 15, wherein said first filter layer comprises a HEPA filter, and said second filter layer comprises one of: a HEPA filter and a filter with higher particle filtration than said first filter layer.

17. The self-sterilizing air filter unit according to claim 16, wherein said second filter layer comprises a filter with greater particle filtration than said first filter layer.

18. The self-sterilizing air filter unit according to claim 17, wherein said air filter unit comprises a coarse filter layer disposed upstream of said heater.

19. The self-sterilizing air filter unit according to claim 13, wherein said filter layers are configured to filter up to 99.9% of airborne particles and microorganisms having a size of 0.1 micrometers to 0.3 micrometers from the air flowing through said air filter unit.

20. The self-sterilizing air filter unit according to claim 13, wherein said filter layers are configured to filter up to 99.999% of airborne particles and microorganisms having a size of 0.1 micrometers to 0.3 micrometers, viruses, bacteria, mite eggs and precipitates, and pollen, from the air flowing through said air filter unit.

* * * * *